(12) United States Patent
Yeoh

(10) Patent No.: US 10,166,156 B2
(45) Date of Patent: Jan. 1, 2019

(54) DIAPER CORE WITH TRIPLE LEAK GUARD

(71) Applicant: SJ CIRCLE SDN BHD, Kulim, Kedah Dami Aman (MY)

(72) Inventor: Sew Jin Yeoh, Butterworth (MY)

(73) Assignee: SJ CIRCLE SDN BHD, Kulim (MY)

( * ) Notice: Subject to any disclaimer, the term of this patent is extended or adjusted under 35 U.S.C. 154(b) by 182 days.

(21) Appl. No.: 15/394,291

(22) Filed: Dec. 29, 2016

(65) Prior Publication Data

US 2017/0189246 A1    Jul. 6, 2017

(30) Foreign Application Priority Data

Dec. 31, 2015  (MY) .............................. PI2015704851

(51) Int. Cl.
| | |
|---|---|
| A61F 13/15 | (2006.01) |
| A61F 13/20 | (2006.01) |
| A61F 13/534 | (2006.01) |
| A61F 13/539 | (2006.01) |
| A61F 13/475 | (2006.01) |
| A61F 13/49 | (2006.01) |
| A61F 13/494 | (2006.01) |

(52) U.S. Cl.
CPC .... *A61F 13/53418* (2013.01); *A61F 13/4755* (2013.01); *A61F 13/49017* (2013.01); *A61F 13/4942* (2013.01); *A61F 13/49446* (2013.01); *A61F 13/539* (2013.01); *A61F 13/53409* (2013.01); *A61F 2013/5349* (2013.01); *A61F 2013/53908* (2013.01); *A61F 2013/53991* (2013.01)

(58) Field of Classification Search
CPC .......... A61F 13/53409; A61F 13/53418; A61F 13/539; A61F 2013/5349; A61F 2013/53908; A61F 13/4755; A61F 13/49017; A61F 13/4942; A61F 13/49446
See application file for complete search history.

(56) References Cited

U.S. PATENT DOCUMENTS

| | | | |
|---|---|---|---|
| 2017/0049636 A1* | 2/2017 | Hardie | A61F 13/4752 |
| 2017/0189243 A1* | 7/2017 | Yeoh | A61F 13/15593 |
| 2018/0098896 A1* | 4/2018 | Hardie | A61F 13/15203 |

* cited by examiner

*Primary Examiner* — Michele M Kidwell
(74) *Attorney, Agent, or Firm* — Hamre, Schumann, Mueller & Larson, P.C.

(57) ABSTRACT

The present invention generally relates to a diaper core, specifically a triple leak guard diaper core (1) for infant and adult, comprising: a center core (10) comprising liquid absorbing material (12) and a plurality of hollow sections (14) disposed on the core (10) longitudinally, allowing the core (10) to bend upward or forming a U-channel, and a center core top surface (CCTS) is provided facing a liquid discharge source (16); at least one layer of bottom core wrap (16) encapsulates the center core (10) with a bottom core gap (BCG) disposed on the center core top surface (CCTS); at least one layer of top core wrap (18) is disposed on the bottom core gap (BCG) and the bottom core wrap (16); and at least one layer of acquisition distribution layer (20) is disposed on the top core wrap (18).

8 Claims, 7 Drawing Sheets

Figure 5:
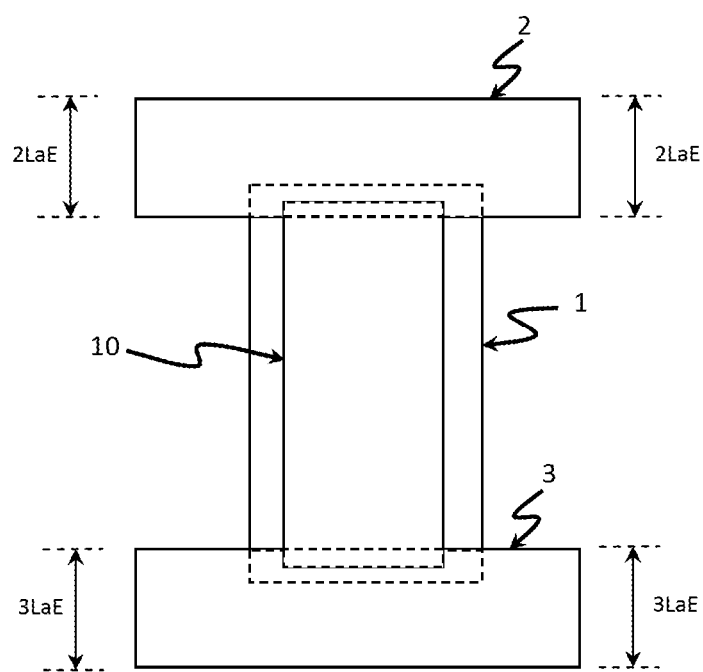

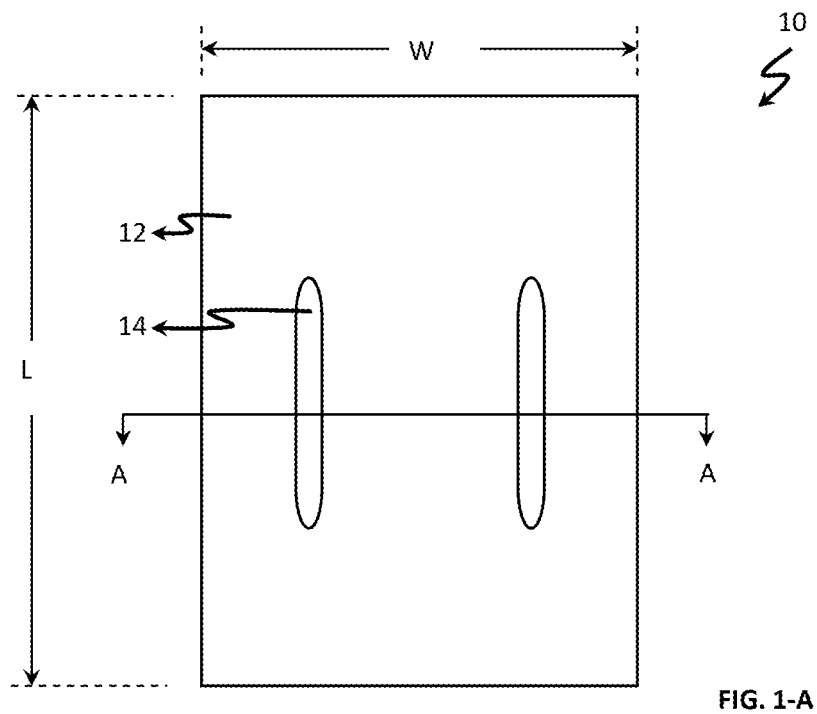
FIG. 1-A
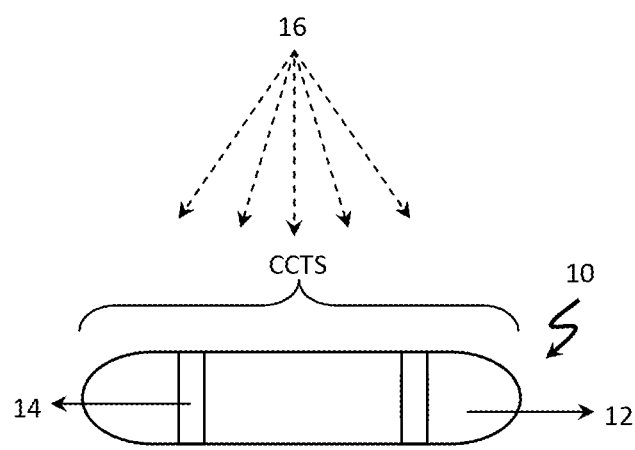
FIG. 1-B

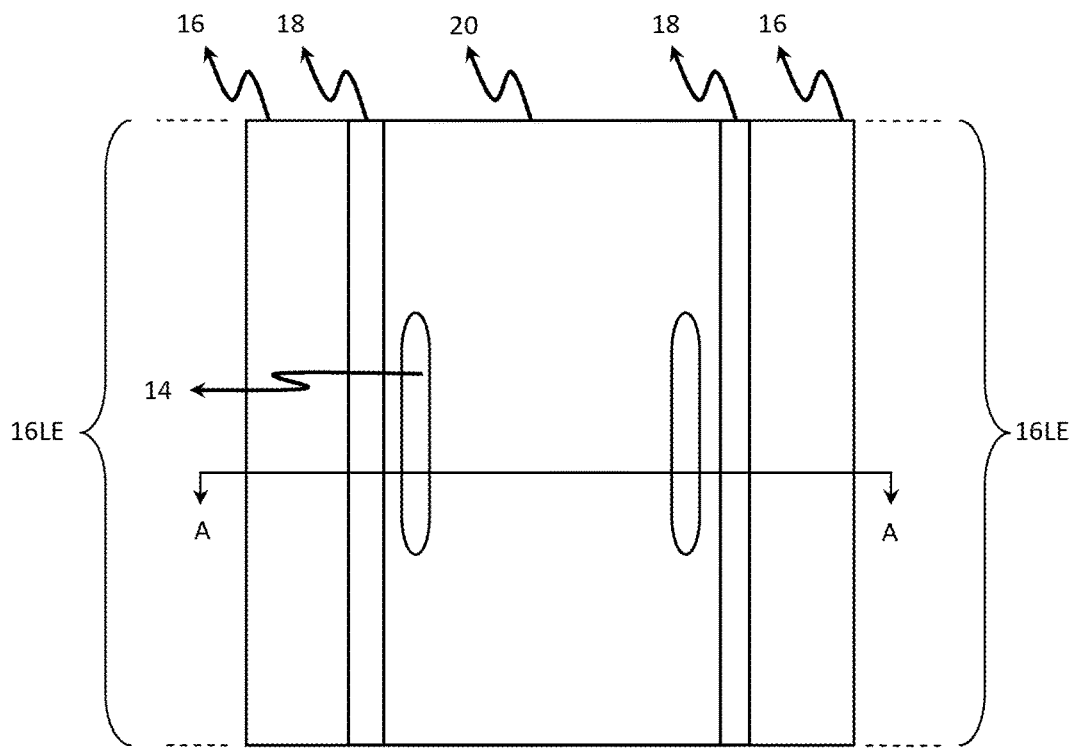
FIG. 2-A
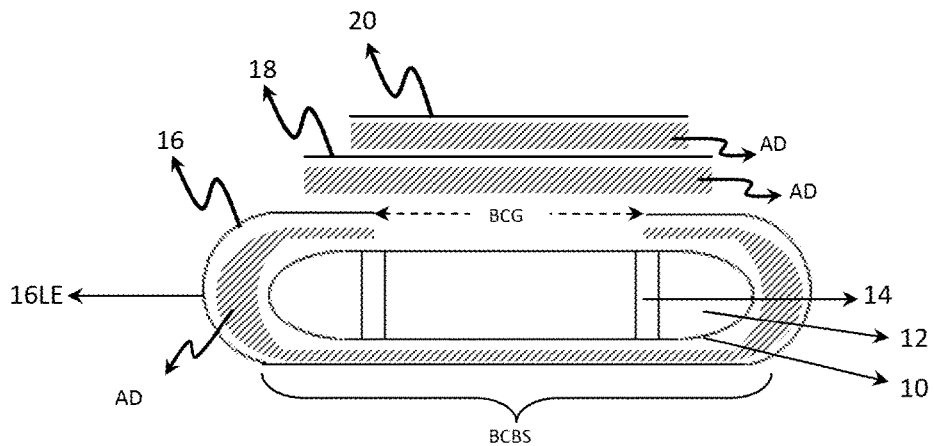
FIG. 2-B

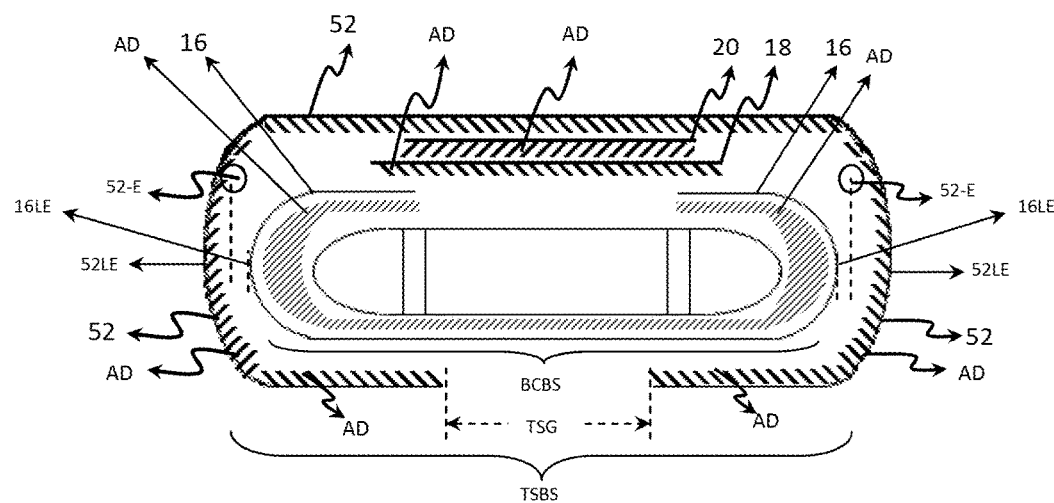
FIG. 2-C
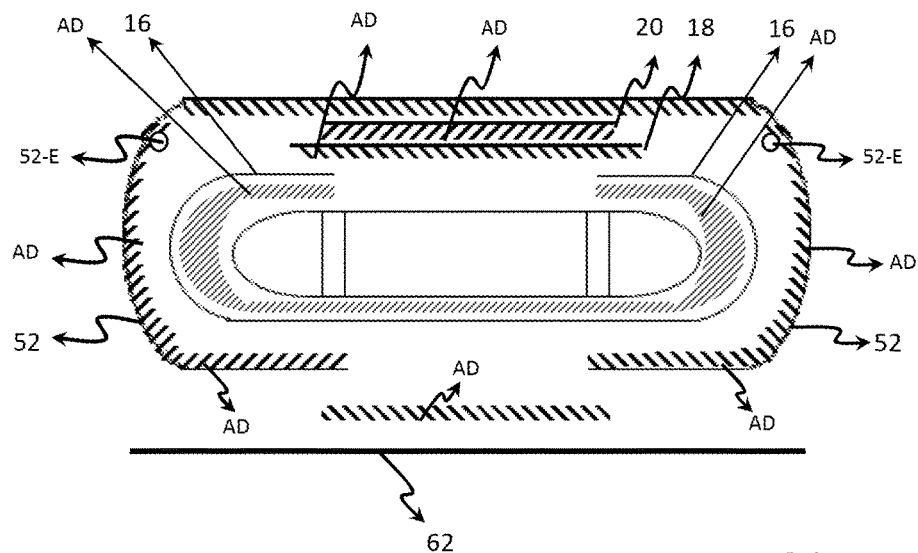
FIG. 2-D

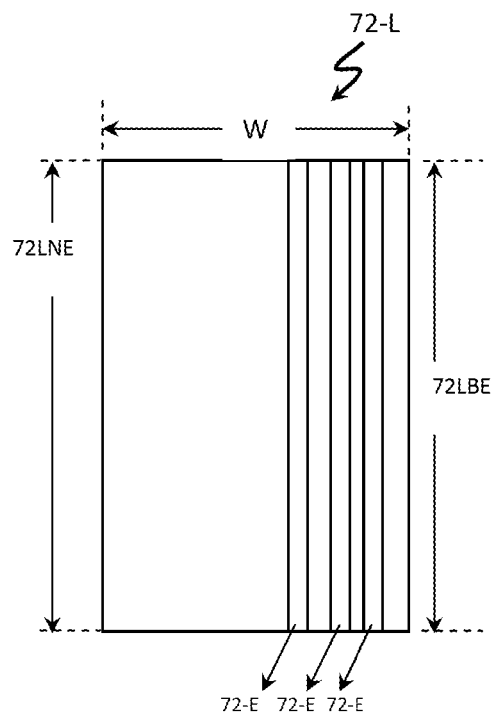
FIG. 2-E
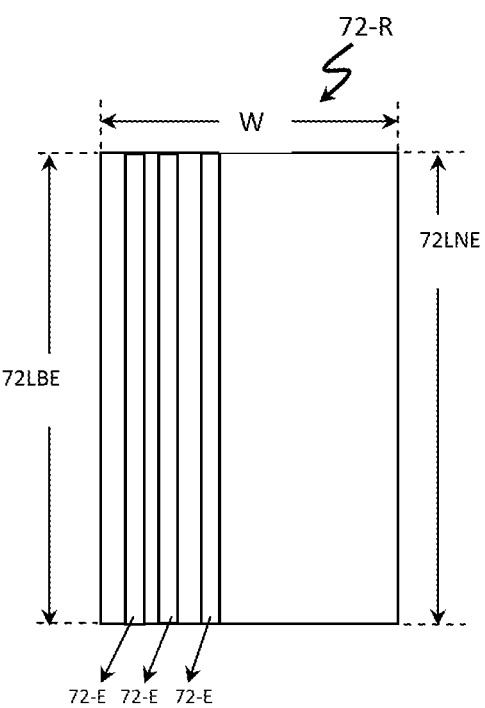
FIG. 2-F
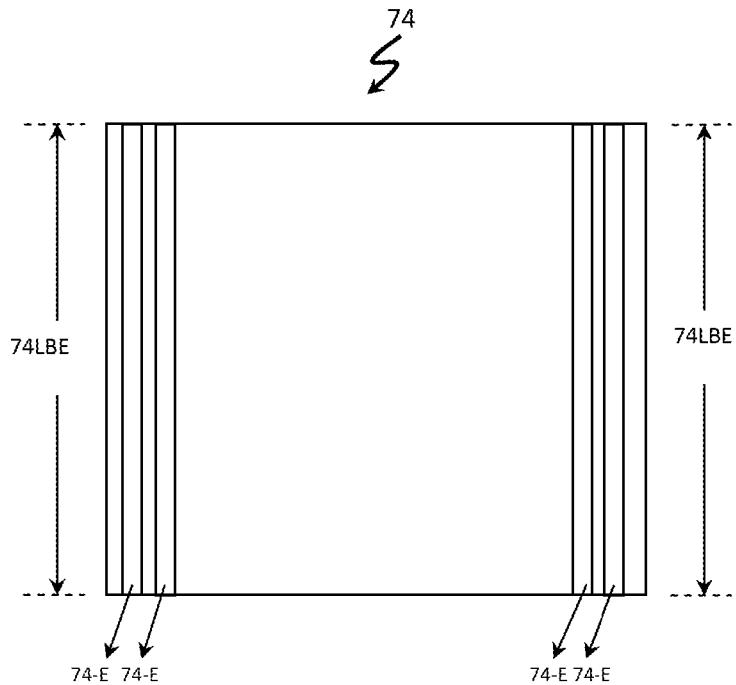
FIG. 2-G

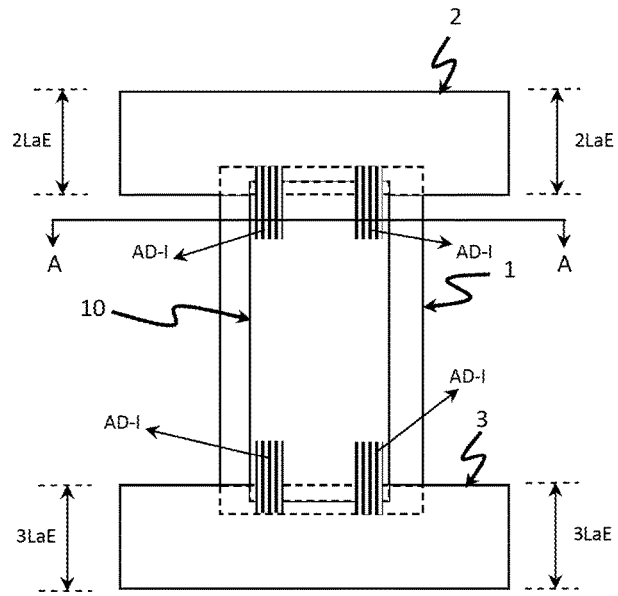
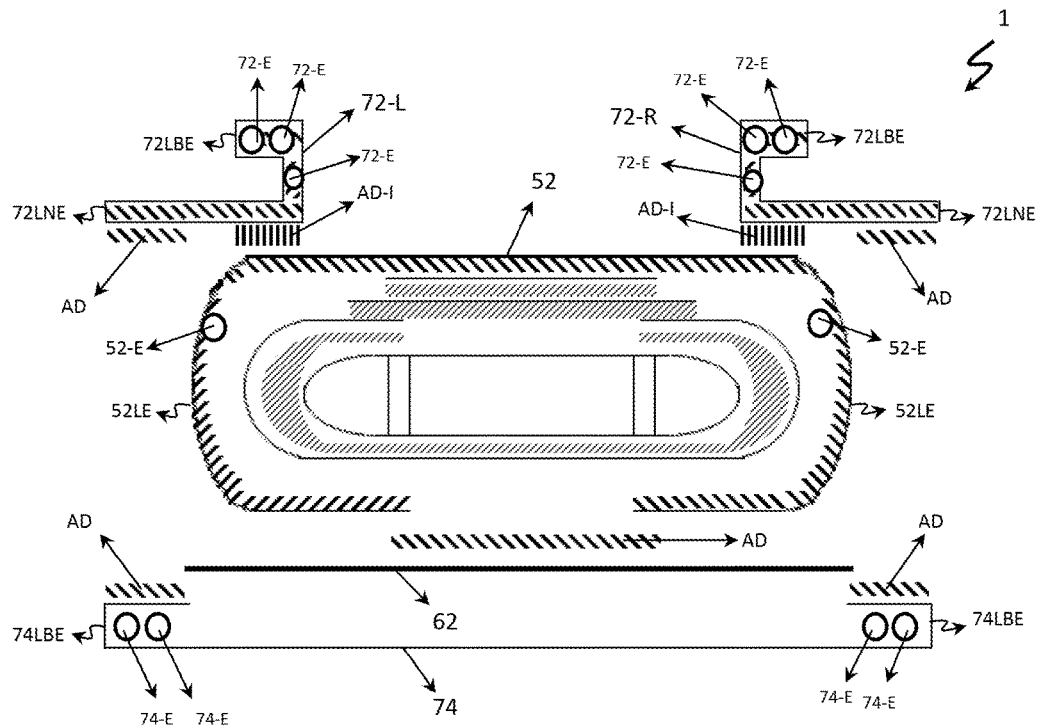
FIG. 3-A
FIG. 3-B

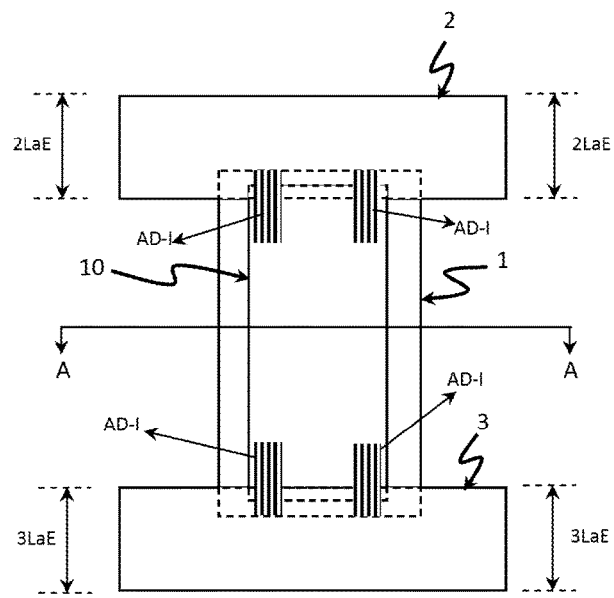
FIG. 4-A
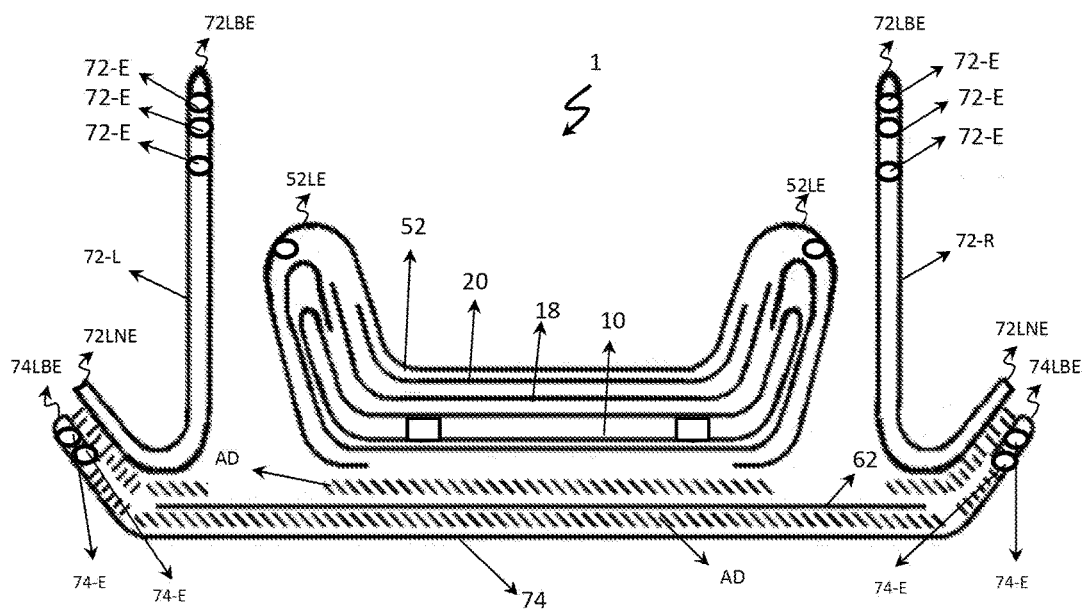
FIG. 4-B

DIAPER CORE WITH TRIPLE LEAK GUARD

1. TECHNICAL FIELD OF THE INVENTION

The present invention generally relates to a diaper core, specifically a triple leak guard diaper core for infant and adult, comprising: a center core comprising liquid absorbing material and a plurality of hollow sections disposed on the core longitudinally, allowing the core to bend upward or forming a U-channel, and a center core top surface is provided facing a liquid discharge source; at least one layer of top core wrap is disposed on the bottom core gap and the bottom core wrap; and at least one layer of acquisition distribution layer is disposed on the top core wrap.

2. BACKGROUND OF THE INVENTION

Numerous diapers with leak guard are well known to provide additional leak protection for the wearer. The leak guards are generally provided further away from the leak source, therefore, they are less effective during in case of a heavy leak. Hence, to alleviate these shortcomings, the present invention discloses a third or triple leak guard which is disposed closest to the leak source, to mitigate or to reduce the diaper core leak.

3. SUMMARY OF THE INVENTION

Accordingly, it is the primary aim of the present invention to provide a third or triple leak guard on a diaper core or absorbent core to enhance the leak protection for the wearer.

It is yet an object of the present invention to provide a third or triple leak guard on the diaper core.

It is yet an object of the present invention to provide a third leak guard that couple with its adjacent leak guard.

According to the preferred embodiment of the present invention the following is provided, A triple leak guard diaper core (1) for infant and adult, comprising:

a center core (10) comprising liquid absorbing material (12) and a plurality of hollow sections (14) disposed on the center core (10) longitudinally, allowing the center core (10) to bend upward or forming a U-channel, and a center core top surface (CCTS) is provided facing a liquid discharge source (16);

at least one layer of bottom core wrap (16) encapsulates the center core (10) with a bottom core gap (BCG) disposed on the center core top surface (CCTS); and at least one layer of acquisition distribution layer (20) is disposed on the top core wrap (18);

characterized in that the bottom core wrap (16) is provided a bottom core bottom surface (BCBS) disposed opposite of the bottom core gap (BCG);

a third leak guard comprising at least one layer of non-woven top sheet (52) encapsulating the bottom core wrap (16), top core wrap (18), and acquisition distribution layer (20);

at least one second leak guard (72-L, 72-R) comprising at least one layer of non-woven with at least one elastic band (72-E) embedded therein; and at least one first leak guard (74) comprising at least one layer of non-woven with at least one elastic band (74-E) embedded therein, is disposed over a top sheet bottom surface (TSBS);

further characterized in that the non-woven top sheet (52) comprising at least one elastic band (52-E) disposed outside of a bottom core wrap longitudinal edge (16LE) and a top sheet bottom surface (TSBS), the top sheet bottom surface (TSBS) comprising a top sheet gap (TSG) disposed over the bottom core bottom surface (BCBS); and at least one PE film (62) is disposed on the top sheet gap (TSG).

4. BRIEF DESCRIPTION OF THE DRAWINGS

Other aspect of the present invention and their advantages will be discerned after studying the Detailed Description in conjunction with the accompanying drawings in which:

FIG. 1-A shows an exemplary top view of an absorbent/center core of a diaper.

FIG. 1-B shows a cross sectional view of the absorbent/center core of a diaper across plane A-A of FIG. 1-A.

FIG. 2-A shows an exemplary top view of a layer of bottom core wrap encapsulating the absorbent core, follow by a layer of top core wrap, and a layer of ADL (acquisition distribution layer).

FIG. 2-B shows a cross sectional view absorbent/center core, bottom core wrap, top core wrap, and ADL across plane A-A of FIG. 2-A.

FIG. 2-C shows a cross sectional view of a layer of non-woven top sheet with elastic band encapsulating the absorbent core, bottom core wrap, top core wrap, and ADL.

FIG. 2-D shows a cross sectional view of a layer of PE film is disposed on the bottom surface of the non-woven top sheet.

FIG. 2-E shows a top view of a layer non-woven comprising elastic bands to make left side of a second leak guard.

FIG. 2-F shows a top view of a layer non-woven comprising elastic bands to make right side of a second leak guard.

FIG. 2-G shows a top view of a layer of non-woven comprising elastic bands to make a first leak guard.

FIG. 3-A shows a top view of coupling of first, second, and third leak guard with locations of an intermittent adhesive.

FIG. 3-B shows a cross sectional view of coupling of first, second, and third leak guard with locations of an intermittent adhesive across plane A-A of FIG. 3-A.

FIG. 4-A shows a top view of coupling of first, second, and third leak guard with locations of continuous adhesive.

FIG. 4-B shows a cross sectional view of coupling of first, second, and third leak guard with locations of continuous adhesive across plane A-A of FIG. 4-A.

FIG. 5 shows a top view of the diaper core merges with an anterior portion and a posterior portion to form a complete diaper.

5. DETAILED DESCRIPTION OF THE DRAWINGS

In the following detailed description, numerous specific details are set forth in order to provide a thorough understanding of the invention. However, it will be understood by the person having ordinary skill in the art that the invention may be practised without these specific details. In other instances, well known methods, procedures and/or components have not been described in detail so as not to obscure the invention.

The invention will be more clearly understood from the following description of the embodiments thereof, given by way of example only with reference to the accompanying drawings, which are not drawn to scale.

Referring to FIG. 1, there is shown an exemplary top view of an absorbent core or a center core (10) of a diaper (1). The center core (10) comprising liquid absorbing material (12) and a plurality of hollow sections (14) disposed on the center core (10) longitudinally, allowing the center core (10) to bend upward or forming a U-channel. The liquid absorbing material (12) comprising fluff core with superabsorbent polymer (SAP). Referring now to FIG. 1-B, there is shown the center core top surface (CCTS) is provided facing a liquid discharge source (16).

Referring now to FIGS. 2-A and 2-B, there are shown at least one layer of non-woven bottom core wrap (16) encapsulates the center core (10) with a bottom core gap (BCG) disposed on the center core top surface (CCTS), at least one layer of non-woven top core wrap (18) is disposed on the bottom core gap (BCG, demarcated by dotted double-arrow line) and the bottom core wrap (16); and at least one layer of acquisition distribution layer (20) is disposed on the top core wrap (18). The bottom core wrap (16) is provided a bottom core bottom surface (BCBS, demarcated by a bracket), is disposed opposite of the bottom core gap (BCG).

Referring to FIG. 2-C, there is shown a third leak guard comprising at least one layer of non-woven top sheet (52) encapsulating the bottom core wrap (16), top core wrap (18), and acquisition distribution layer (20). The non-woven top sheet (52) comprising at least one elastic band (52-E) disposed outside of a bottom core wrap longitudinal edge (16LE) and a top sheet bottom surface (TSBS, demarcated by bracket); the top sheet bottom surface (TSBS) comprising a top sheet gap (TSG, demarcated by dotted double-arrow line) disposed over the bottom core bottom surface (BCBS). Then, referring now to FIG. 2-D, at least one PE film (62) is disposed on the top sheet gap (TSG) and top sheet bottom surface (TSBS).

Referring to FIGS. 2-E and 2-F, there are shown one second leak guard (72-L, 72-R), comprising at least one layer of non-woven sheet with at least one elastic band (72-E) embedded therein whereby the bands (72-E) are preferably arranged on the sheet (72-L, 72-R) one of the longitudinal edge (72LBE). Whereas, the other longitudinal edges (72LNE) the second leak guard (72-L, 72-R) have no elastic bands embedded therein.

Referring to FIG. 2-G, there is shown at least one first leak guard (74) comprising at least one layer of non-woven sheet with at least one elastic band (74-E) embedded therein whereby the bands (74-E) are preferably arranged on the sheet (74) both longitudinal edges (74LE), the leak guard (74) is disposed over a top sheet bottom surface (TSBS).

Referring now to FIGS. 3-A, 3-B, 4-A, and 4-B, the second leak guard (72-L, 72-R) longitudinal edges (72LBE) comprising elastic bands (74-E), are disposed adjacent of the non-woven top sheet (52) top sheet longitudinal edges (52LE) by adhesive (AD), or intermittent adhesive (AD-I), or a combination thereof. The second leak guard (72-L, 72-R) longitudinal edges (72LNE) with no elastic bands, couple with the first leak guard (74) longitudinal edges (74LBE) with elastic bands (74-E) by adhesive (AD). The first leak guard (74) is disposed over a top sheet bottom surface (TSBS).

Referring now to FIG. 5, there is shown the core (1) capable of couple with a diaper anterior portion (2) which is worn on an infant or adult's anterior pelvic region. The core (1) is also capable of coupling with a diaper posterior portion (3) which is worn on an infant or adult's anterior pelvic region. Moreover, the anterior portion (2) lateral edges (2LaE) couple with posterior portion (3) lateral edges (3LaE) by means of adhesive, or heat sealing, or ultrasonic sealing, or a combination thereof.

While the present invention has been shown and described herein in what are considered to be the preferred embodiments thereof, illustrating the results and advantages over the prior art obtained through the present invention, the invention is not limited to those specific embodiments. Thus, the forms of the invention shown and described herein are to be taken as illustrative only and other embodiments may be selected without departing, from the scope of the present invention, as set forth in the claims appended hereto.

What is claimed is:

1. A triple leak guard diaper core for infant and adult, comprising:
    a center core comprising liquid absorbing material and a plurality of hollow sections disposed on the core longitudinally, allowing the core to bend upward or forming a U-channel, and a center core top surface is provided facing a liquid discharge source;
    at least one layer of bottom core wrap encapsulates the center core with a bottom core gap disposed on the center core top surface; and
    at least one layer of acquisition distribution layer is disposed on the top core wrap;
    wherein
    the bottom core wrap is provided a bottom core bottom surface disposed opposite of the bottom core gap;
    a third leak guard comprising at least one layer of non-woven top sheet encapsulating the bottom core wrap, top core wrap, and acquisition distribution layer;
    at least one second leak guard comprising at least one layer of non-woven with at least one elastic band embedded therein; and
    at least one first leak guard comprising at least one layer of non-woven with at least one elastic band embedded therein, is disposed over a top sheet bottom surface;
    wherein
    the non-woven top sheet comprising at least one elastic band disposed outside of a bottom core wrap longitudinal edge and a top sheet bottom surface, the top sheet bottom surface comprising a top sheet gap disposed over the bottom core bottom surface; and
    at least one PE film is disposed on the top sheet gap and top sheet bottom surface.

2. The triple leak guard diaper core for infant and adult as claimed in claim 1 wherein the second leak guard are disposed on the non-woven top sheet top sheet longitudinal edges by adhesive, or intermittent adhesive, or a combination thereof.

3. The triple leak guard diaper core for infant and adult as claimed in claim 1 wherein the second leak guard longitudinal edge couple with the first leak guard longitudinal edges by adhesive.

4. The triple leak guard diaper core for infant and adult as claimed in claim 1 wherein the first leak guard is disposed over a top sheet bottom surface.

5. The triple leak guard diaper core for infant and adult as claimed in claim 1 wherein the core capable of couple with a diaper anterior portion which is worn on an infant or adult's anterior pelvic region.

6. The triple leak guard diaper core for infant and adult as claimed in claim 5 wherein the core capable of couple with a diaper posterior portion which is worn on an infant or adult's anterior pelvic region.

7. The triple leak guard diaper core for infant and adult as claimed in claim 5 wherein the anterior portion lateral edges couple with posterior portion lateral edges by means of adhesive, or heat sealing, or ultrasonic sealing, or a combination thereof.

8. The triple leak guard diaper core for infant and adult as claimed in claim 1 wherein the bottom core wrap and the bottom core gap have at least one layer of non-woven top core wrap disposed thereon.

\* \* \* \* \*